(12) United States Patent
Inoue (10) Patent No.: US 11,260,205 B2
(45) Date of Patent: Mar. 1, 2022

(54) GUIDE WIRE

(71) Applicant: TERUMO KABUSHIKI KAISHA, Tokyo (JP)

(72) Inventor: Shuhei Inoue, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 337 days.

(21) Appl. No.: 16/155,374

(22) Filed: Oct. 9, 2018

(65) Prior Publication Data

US 2019/0046774 A1 Feb. 14, 2019

Related U.S. Application Data

(63) Continuation of application No. PCT/JP2017/024562, filed on Jul. 4, 2017.

(30) Foreign Application Priority Data

Aug. 17, 2016 (JP) .............................. JP2016-159989

(51) Int. Cl.
*A61M 25/09* (2006.01)

(52) U.S. Cl.
CPC ... *A61M 25/09* (2013.01); *A61M 2025/09083* (2013.01); *A61M 2025/09133* (2013.01)

(58) Field of Classification Search
None
See application file for complete search history.

(56) References Cited

U.S. PATENT DOCUMENTS

| | | | | |
|---|---|---|---|---|
| 4,796,642 A | * | 1/1989 | Harris | ..................... A61N 1/056 |
| | | | | 600/434 |
| 4,934,380 A | | 6/1990 | De Toledo | |
| | | | (Continued) | |

FOREIGN PATENT DOCUMENTS

| CN | 1827187 A | 9/2006 |
|---|---|---|
| CN | 101384293 A | 3/2009 |
| | (Continued) | |

OTHER PUBLICATIONS

International Search Report (PCT/ISA/210) dated Sep. 26, 2017, by the Japanese Patent Office as the International Searching Authority for International Application No. PCT/JP2017/024562.

(Continued)

*Primary Examiner* — Sean P Dougherty
*Assistant Examiner* — Benjamin S Melhus
(74) *Attorney, Agent, or Firm* — Buchanan Ingersoll & Rooney PC (57) ABSTRACT

A guide wire including a flexible first core wire which has a first plate-shaped portion having a plate shape and a first linear portion having a linear shape that is continuous to the first-plate shaped portion. The width of the first plate-shaped is larger than the width of the first linear portion. The guide wire includes a flexible second core wire which has a second plate-shaped portion having a plate shape and a second linear portion having a linear shape that is continuous to the second-plate shaped portion. The width of the second plate-shaped portion is larger than the width of the second linear portion. The second plate-shaped portion axially overlaps the first linear portion, and the second linear portion axially overlaps the first plate-shaped portion.

23 Claims, 6 Drawing Sheets

(56) References Cited

U.S. PATENT DOCUMENTS

| | | | |
|---|---|---|---|
| 5,230,348 A | | 7/1993 | Ishibe et al. |
| 5,299,580 A | * | 4/1994 | Atkinson ............... A61M 25/09 |
| | | | 600/585 |
| 5,358,479 A | * | 10/1994 | Wilson ............... A61M 25/0136 |
| | | | 600/434 |
| 5,365,942 A | * | 11/1994 | Shank ................... A61M 25/09 |
| | | | 600/434 |
| 5,824,031 A | | 10/1998 | Cookston et al. |
| 6,290,656 B1 | | 9/2001 | Boyle et al. |
| 6,890,329 B2 | * | 5/2005 | Carroll ............... A61M 25/0041 |
| | | | 604/528 |
| 7,955,298 B2 | * | 6/2011 | Carroll ............... A61M 25/0041 |
| | | | 604/95.04 |
| 8,376,961 B2 | * | 2/2013 | Layman ................. A61M 25/09 |
| | | | 600/585 |
| 8,500,656 B2 | * | 8/2013 | Lupton ............ A61M 25/09041 |
| | | | 600/585 |
| 2006/0241419 A1 | | 10/2006 | Satou et al. |
| 2007/0244413 A1 | | 10/2007 | Biggins |
| 2008/0154207 A1 | | 6/2008 | Hardin |
| 2008/0234606 A1 | | 9/2008 | Itou |
| 2008/0306468 A1 | | 12/2008 | Tamai et al. |
| 2010/0087780 A1 | | 4/2010 | Tekulve et al. |
| 2010/0249654 A1 | | 9/2010 | Elsesser et al. |
| 2010/0318001 A1 | | 12/2010 | Miyata et al. |
| 2012/0197159 A1 | | 8/2012 | Miyata et al. |
| 2012/0245488 A1 | | 9/2012 | Matsumoto |
| 2013/0110002 A1 | | 5/2013 | Miyata et al. |
| 2013/0253374 A1 | | 9/2013 | Simpson et al. |
| 2015/0238734 A1 | | 8/2015 | Kanazawa |
| 2016/0022215 A1 | | 1/2016 | Henderson et al. |
| 2016/0331943 A1 | * | 11/2016 | Lupton .................. A61B 17/22 |
| 2017/0106172 A1 | | 4/2017 | Ootani et al. |

FOREIGN PATENT DOCUMENTS

| | | |
|---|---|---|
| CN | 101920055 A | 12/2010 |
| CN | 102614572 A | 8/2012 |
| CN | 102688552 A | 9/2012 |
| CN | 103083785 A | 5/2013 |
| CN | 104857613 A | 8/2015 |
| JP | 02104370 A | 4/1990 |
| JP | 04164459 A | 6/1992 |
| JP | 2002527179 A | 8/2002 |
| JP | 2004-154286 A | 6/2004 |
| JP | 2006271955 A | 10/2006 |
| JP | 2016-064062 A | 4/2016 |
| WO | 03/041784 A2 | 5/2003 |
| WO | 2016/047364 A1 | 3/2016 |

OTHER PUBLICATIONS

An English Translation of the International Search Report (Form PCT/ISA/210) and the Written Opinion of the International Searching Authority (Form PCT/ISA/237) dated Sep. 26, 2017, by the Japanese Patent Office in corresponding International Application No. PCT/JP2017/024562. (6 pages).

The extended European Search Report dated Mar. 26, 2020, by the European Patent Office in corresponding European Patent Application No. 17841300.1-1132. (8 pages).

Office Action (First Office Action) dated Jul. 1, 2020, by the State Intellectual Property Office of People's Republic of China in corresponding Chinese Patent Application No. 201780026227.5 and an English Translation of the Office Action. (12 pages).

\* cited by examiner

GUIDE WIRE

CROSS-REFERENCES TO RELATED APPLICATIONS

This application is a continuation of International Application No. PCT/JP2017/024562 filed on Jul. 4, 2017, and claims priority to Japanese Patent Application No. 2016-159989 filed on Aug. 17, 2016, the entire content of both of which is incorporated herein by reference.

TECHNICAL FIELD

The present invention generally relates to a guide wire.

BACKGROUND ART

The guide wire is used for introducing a catheter into a target site. The catheter introduced along the guide wire may be used for treatment of a site in which a surgical operation is relatively difficult, treatment using relatively low invasion to a human body, examination of angiography in cardiac diseases and treatment thereof, and the like at the target site.

For example, a guide wire used for a percutaneous coronary intervention (PCI) is inserted together with a balloon catheter to a front side of a stenosis of a coronary artery which is the target site. The insertion occurs in a state in which a distal end of the guide wire is caused to protrude from a distal end of the balloon catheter while this state may be viewed using X-ray fluoroscopy. Next, the guide wire induces (introduces) the distal portion of the balloon catheter to the vicinity of the stenosis.

It is preferable that the guide wire used in such an operation be excellent in flexibility and restorability (i.e., relatively flexible and relatively resilient in restoring the shape of the guide wire) and relatively successful in torque transmission performance in which the torque from a hand portion is effectively transmitted to the distal portion of the guide wire. The characteristics of the guide wire are important for inducing a treatment device such as a balloon catheter to a target site in a (relatively) complicatedly bent blood vessel.

In some cases, the guide wire used for the PCI may perform the shaping at the distal portion of the core wire of the guide wire for the purpose of enhancing the blood vessel selectivity (i.e., the distal portion of the core wire may be configured to deform into an appropriate shape (e.g., a curved or bent shape) by applying an external force before inserting the core wire into the blood vessel and then retain the appropriate shape (e.g., a curved or bent shape) after insertion into the blood vessel). It is known that the distal portion of the core wire is formed into a flat plate shape as disclosed, for example, in U.S. Patent Application Publication No. 2008/0234606 in order to facilitate the shaping. However, when the distal portion of the core wire is formed in a flat plate shape, the rigidity of the distal portion of the core wire is lowered, and the torque transmission performance of the guide wire is lowered. There is also a limit to the length for making it possible to set the core wire in a flat plate shape, and there is a problem that the range that can be shaped is limited.

SUMMARY OF INVENTION

The guide wire disclosed here seeks to achieve both (relatively) excellent torque transmission performance and (relatively) excellent shaping property.

An aspect of the disclosure involves a guide wire including a flexible first core wire, and a flexible second core wire configured separately from the first core wire, in which the first core wire has a first plate-shaped portion having a plate shape, and a first linear portion provided continuously on a proximal side of the first plate-shaped portion and having a linear shape thinner than the first plate-shaped portion, and the second core wire has a second plate-shaped portion having a plate shape and disposed to overlap the first linear portion, and a second linear portion that is provided continuously on a distal side of the second plate-shaped portion, has a linear shape thinner than the second plate-shaped portion, and is disposed to overlap the first plate-shaped portion.

The second core wire of the guide wire may be shorter than the first core wire, and at least a distal portion and a proximal portion of the second core wire can be fixed with respect to the first core wire.

A length from a distal end of the first plate-shaped portion to a proximal end of the second plate-shaped portion along a longitudinal direction of the wire is 0.5 mm or more and 250 mm or less in some embodiments of the guide wire.

The first plate-shaped portion and the second plate-shaped portion are flat plates in a natural state in which no external force is applied, and a normal line of the first plate-shaped portion and a normal line of the second plate-shaped portion are directed in the same direction in some embodiments of the guide wire.

The center of the cross-sectional shape of the first linear portion and the center of the cross-sectional shape of the second linear portion are in a coaxial state positioned coaxially along the longitudinal direction of the wire in some embodiments of the guide wire.

Some embodiments of the guide wire include a positioning portion which maintains the coaxial state.

The positioning portion may include a first groove which is formed in the first plate-shaped portion and into which the second linear portion is inserted, and a second groove which is formed in the second plate-shaped portion and into which the first linear portion is inserted.

The cross-sectional shape of the first linear portion and the cross-sectional shape of the second linear portion have the same shape in some embodiments of the guide wire.

The cross-sectional shape of the first linear portion and the cross-sectional shape of the second linear portion are circular or semicircular in some embodiments of the guide wire.

The second core wire has a third linear portion that is provided continuously on the proximal side of the second plate-shaped portion, has a linear shape thinner than the second plate-shaped portion, and is disposed to overlap the first linear portion in some embodiments of the guide wire.

In the plan view of the flat plate of the guide wire, it is preferable that the proximal portion of the first plate-shaped portion and the distal portion of the second plate-shaped portion are in contact with each other or overlap each other.

It is also preferable that at least the width of the proximal portion of the first plate-shaped portion of the guide wire gradually decreases toward a proximal end direction.

The cross-sectional shape of the first linear portion and the cross-sectional shape of the second linear portion may be circular or semicircular, and the centers of the circle or the semicircle are preferably in a coaxial state positioned coaxially along the longitudinal direction of the wire.

Additionally, it is preferable to include a coil which covers the first plate-shaped portion and the first linear portion and covers the second plate-shaped portion and the second linear portion.

Each of the first plate-shaped portion and the second plate-shaped portion, which are formed of separate members, serves as a part for shaping, and therefore shaping can be performed relatively easily and relatively reliably.

Also, when torque is applied from the proximal side of the guide wire (e.g., via a user external to the living body), the torque is reliably transmitted to the distal end of the guide wire in the living body because the first linear portion overlaps the second plate-shaped portion and the second linear portion overlaps the first plate-shaped portion.

Further, for example, when shaping is performed and used, it is possible to secure a shapeable range as long as possible (i.e., over as long of an axial extent of the guide wire as possible).

In this manner, it is possible to achieve both (relatively) excellent torque transmission performance and shaping property of the guide wire.

DETAILED DESCRIPTION OF EMBODIMENTS

Set forth below is a detailed description of embodiments with reference to the drawings of a guide wire representing examples of the inventive guide wire disclosed here.

First Embodiment

Figure 1:
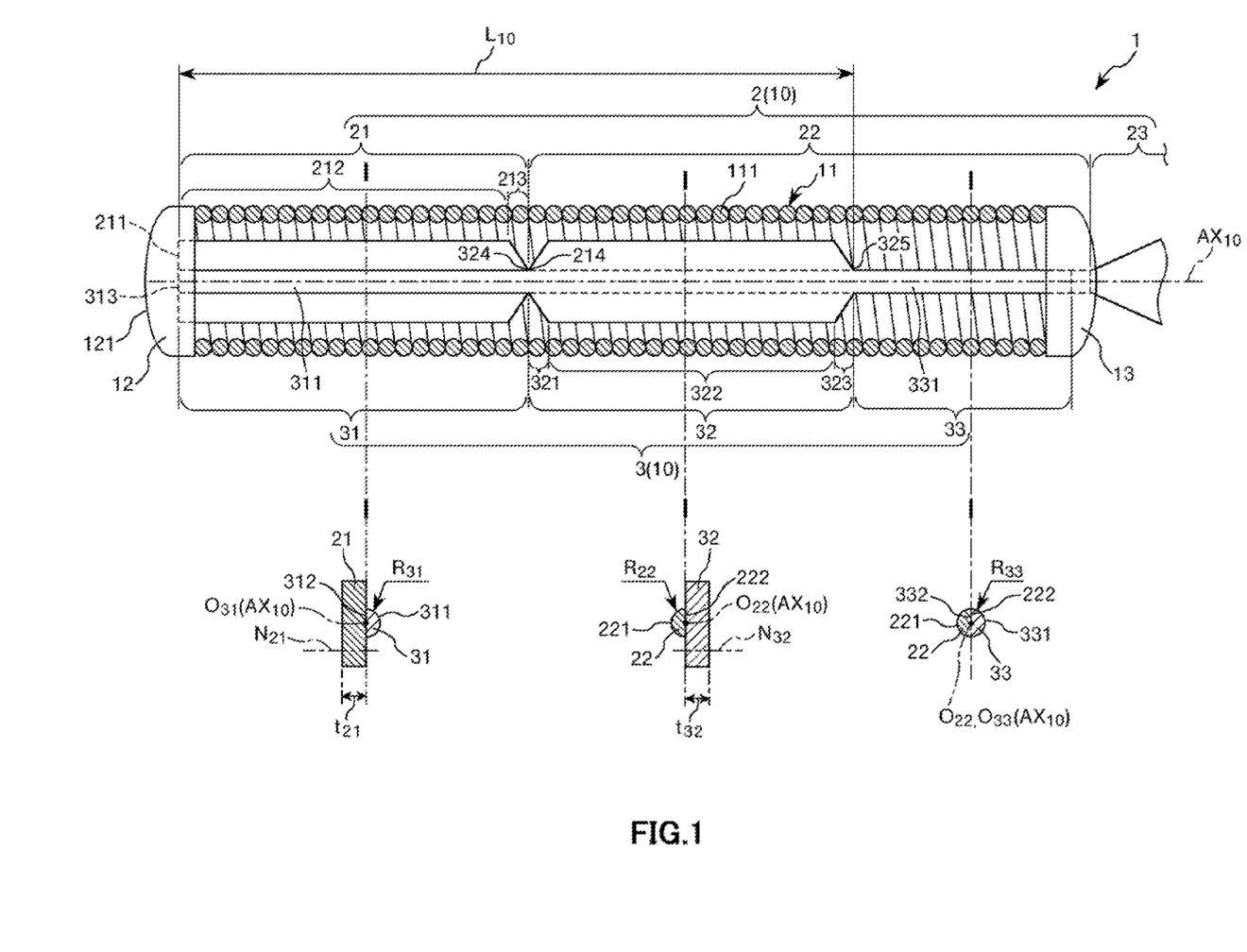
FIG. 1 is a partial longitudinal cross-sectional plan view of a first embodiment of a guide wire and auxiliary cross-sectional views of the first embodiment of the guide wire.
Figure 2:
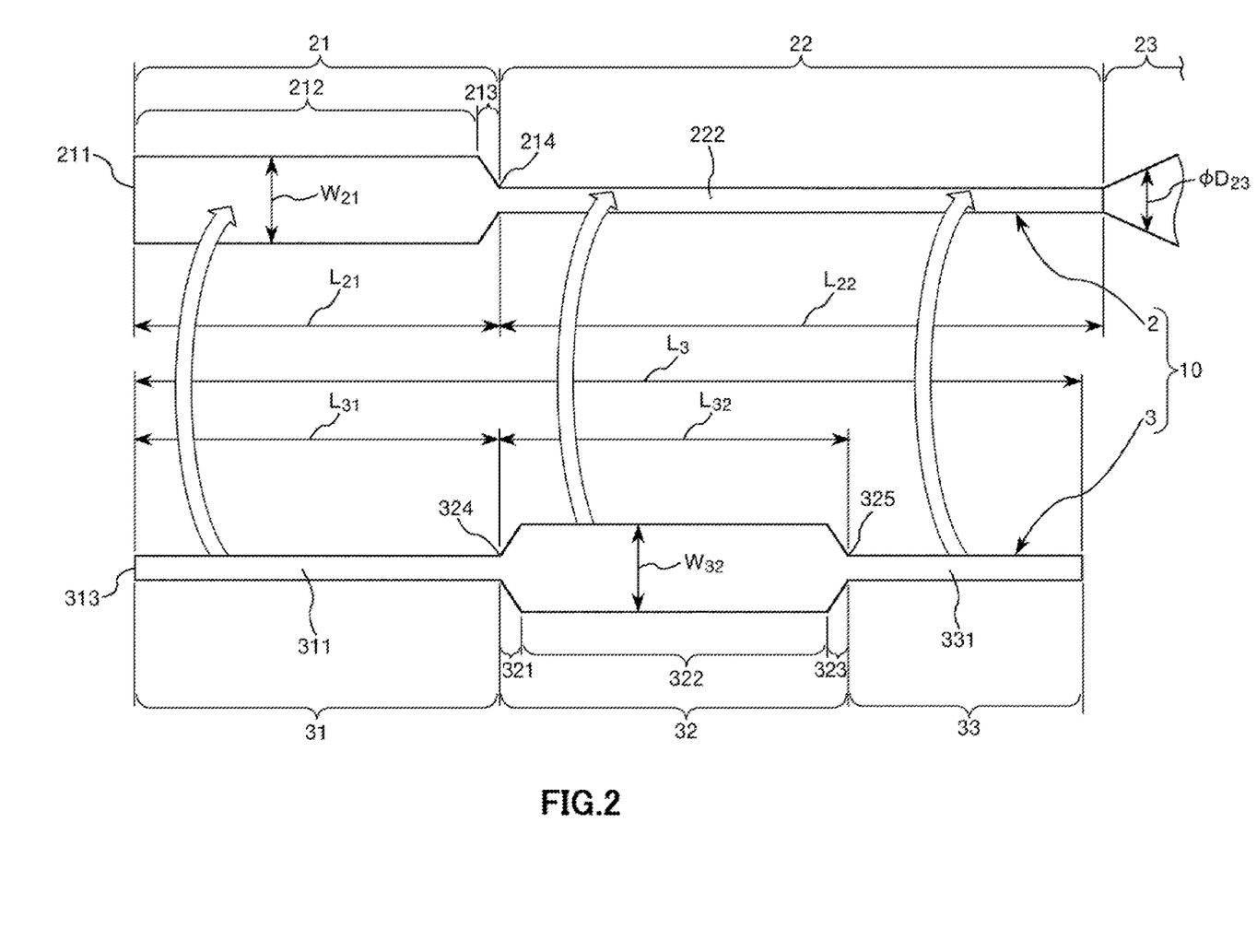
FIG. 2 is an exploded plan view of a first core wire and a second core wire provided in the guide wire illustrated in FIG. 1.

FIG. 1 shows a partial longitudinal cross-sectional plan view and three auxiliary cross-sectional views illustrating a first embodiment of the disclosed guide wire. FIG. 2 is an exploded plan view of a first core wire and a second core wire provided in the guide wire illustrated in FIG. 1. Note that, in the following description, a right side of FIGS. 1 and 2 (the same also applies to FIGS. 3 to 7) is referred to as a "proximal end" or a "proximal side", and a left side is referred to as a "distal end" or a "distal side" for convenience of description. Also, a longitudinal direction of the guide wire is shortened, a radial direction (a thickness direction) of the guide wire is schematically illustrated in an exaggerated manner, and a ratio between the longitudinal direction and the radial direction is different from an actual one in the drawings to facilitate an understanding of the disclosure.

A guide wire 1 illustrated in FIG. 1 is a catheter guide wire used by being inserted into a lumen of a catheter including an endoscope (i.e., a catheter that has an endoscope and a lumen moves along the guide wire with the guide wire in the lumen of the catheter). The guide wire 1 includes a wire main body 10 including a first core wire 2 and a second core wire 3, and a spiral coil 11 which covers a portion of a distal side of the wire main body 10. Although an overall length of the guide wire 1 is not particularly limited, when the guide wire 1 is used for a PCI, for example, the overall length is preferably 200 mm or more and 5000 mm or less, and more preferably 1000 mm or more and 3000 mm or less.

As illustrated in FIGS. 1 and 2, the first core wire 2 is made of an elongated body having flexibility (i.e., the first core wire 2 is a flexible elongated body). The first core wire 2 has a first plate-shaped portion 21, a first linear portion 22, and a tapered portion 23, which are disposed in order from the distal side thereof (i.e., the first plate-shaped portion 21 is at the distal end of the first core wire 2, the first linear portion 22 is directly proximal of the first plate-shaped portion 21, and the tapered portion 23 is directly proximal of the first linear portion 22). It is preferable that, for example, the outer diameter of the portion of the first core wire 2 on the proximal side from the tapered portion 23 is constant.

The first plate-shaped portion 21 is a portion of the first core wire 2 having a plate shape. The first plate-shaped portion 21 is a flat plate in a natural state when no external force is applied as shown in FIG. 1. An overall length $L_{21}$ of the first plate-shaped portion 21 is not particularly limited, and is preferably, for example, 0.5 mm or more and 250.0 mm or less, and more preferably, 0.5 mm or more and 150 mm or less.

The first plate-shaped portion 21 has a constant width portion 212 and a gradually decreasing width portion 213. The constant width portion 212 is a portion of the first plate-shaped portion 21 in which a width $W_{21}$ from the distal portion of the first plate-shaped portion 21 to a predetermined length is constant along a longitudinal direction of the first core wire 2. The gradually decreasing width portion 213 is a portion in which the width $W_{21}$ gradually decreases toward the proximal side at the proximal portion of the first plate-shaped portion 21 (i.e., the distal end of the gradually decreasing width portion 213 is connected to and continuous with the proximal end of the constant width portion 212 and is tapered with a decreasing outer dimension proximally in the axial direction). The width $W_{21}$ of the constant width portion 212 is not particularly limited, and is preferably, for example, 0.080 mm or more and 0.880 mm or less, and more preferably 0.100 mm or more and 0.350 mm or less. A gradually decreasing width portion in which the width $W_{21}$ gradually decreases toward the distal side may be formed at the distal portion of the first plate-shaped portion 21.

The thickness $t_{21}$ of the first plate-shaped portion 21 is constant along the longitudinal direction of the wire (i.e., the constant width portion 212 and the gradually decreasing width portion 213 possess the same thickness). The thickness $t_{21}$ is not particularly limited, and is preferably, for example, 0.015 mm or more and 0.070 mm or less. Although the thickness $t_{21}$ is constant along the longitudinal direction of the first core wire 2 in the embodiment illustrated in FIGS. 1 and 2, the thickness $t_{21}$ is not limited to being constant throughout the axial extent of the first core wire 2. For example, the thickness of the first core wire 2 may gradually decrease (taper) toward the distal side.

The first plate-shaped portion 21 can be bent and deformed into a desired shape together with a second linear portion 31 of the second core wire 3 overlapping the first plate-shaped portion 21, and can be used for shaping. The shaping may also be called "reshaping". The shaping of the first-plate shaped portion 21 of the first core wire 2 and the second linear portion 31 of the second core wire 3 helps make it is possible to easily and reliably select the traveling direction of the guide wire 1 in the living body, and thus, the operability of the guide wire 1 is remarkably improved.

The first linear portion 22 is provided continuously on the proximal side of the first plate-shaped portion 21 (i.e., the distal end of the first linear portion 22 is connected to the proximal end of the first plate-shaped portion 21 so that these two portions 21, 22 are a continuous structure). The first linear portion 22 is a portion having a linear shape that is thinner (i.e., possesses a smaller width in a width direction orthogonal to the axial direction as shown in FIG. 1) than the first plate-shaped portion 21. In the present embodiment, the overall length $L_{22}$ of the first linear portion 22 is longer than the overall length $L_{21}$ of the first plate-shaped portion 21.

As illustrated in FIG. 1, the cross-sectional shape of the first linear portion 22 is semicircular. A radius $R_{22}$ of the first linear portion 22 is constant along the longitudinal direction of the wire. The radius $R_{22}$ is not particularly limited, and is, for example, preferably the same as the thickness $t_{21}$.

The tapered portion 23 is provided continuously on the proximal side of the first linear portion 22 (i.e., the distal end of the tapered portion 23 is connected to the proximal end of the first linear portion 22 so that these two portions 22, 23 are a continuous structure). The tapered portion 23 is a portion in which an outer diameter $\phi D_{23}$ gradually decreases (tapers) toward the distal side as shown in FIG. 2. Therefore, the rigidity of the first core wire 2 can be gradually reduced toward the distal side by the tapered portion 23. Reducing the rigidity toward the distal end may help improve the followability (e.g., maneuverability) of the guide wire 1.

As illustrated in FIGS. 1 and 2, the second core wire 3 is an elongated body having flexibility which is configured separately from the first core wire 2 (i.e., is a separate, distinct structure from the first core wire 2). The second core wire 3 is shorter than the first core wire 2. An overall length $L_3$ of the second core wire 3 is preferably equal to or shorter than the total sum of the overall length $L_{21}$ and the overall length $L_{22}$ of the first core wire 2 (i.e., the length of the first plate-shaped portion 21 and the first linear portion 22 of the first core wire 2).

The distal portion (including the distal end) of the second core wire 3 is fixed to the distal portion of the first core wire 2 via a fixing material 12. The proximal portion (including the proximal end) of the second core wire 3 is fixed to the first core wire 2 in the vicinity of a boundary portion between the first linear portion 22 and the tapered portion 23 of the first core wire 2 via a fixing material 13. It is preferable that each of the fixing material 12 and the fixing material 13 is made of a solder (brazing material), but the fixing materials 12 and/or 13 are not limited thereto, and for example, an adhesive agent may be used. A distal end 121 of the fixing material 12 is preferably rounded in order to prevent in vivo damage (i.e., damage within the living body).

The second core wire 3 has a second linear portion 31, a second plate-shaped portion 32, and a third linear portion 33 disposed in order from the distal side thereof (i.e., the second linear portion 31 is at the distal end of the second core wire 3, the second plate-shaped portion 32 is directly proximal of the second linear portion 31, and the third linear portion 33 is directly proximal of the second plate-shaped portion 32).

The second plate-shaped portion 32 has a plate shape, and is disposed to overlap the first linear portion 22 of the first core wire 2 in the axial direction. That is, the second plate-shaped portion 32 extends along the first linear portion 22 to be in contact with the first linear portion 22 as shown in FIGS. 1 and 2. The overall length $L_{32}$ of the second plate-shaped portion 32 is the same as the overall length $L_{21}$ of the first plate-shaped portion 21 in the present embodiment.

The second plate-shaped portion 32 is a portion which is bent and deformed into a desired shape together with the first linear portion 22 overlapping (in the axial direction) the second plate-shaped portion 32. The second plate-shaped portion 32 (together with the first linear portion 22) can be used for shaping in the same manner as the first plate-shaped portion 21. As described above, the first plate-shaped portion 21 and the second plate-shaped portion 32 of the guide wire 1, which are made of separate members, are portions responsible for shaping, respectively. As shown in FIG. 1, the cross-sectional shape of the first plate-shaped portion 21 and the second-plate shaped portion 32 may be equivalent (the shapes are "equivalent" in that they possess the same shape (even if oriented differently, e.g., mirror images) and the same cross-sectional area).

As described above, the distal portion of the second core wire 3 is fixed to the first core wire 2 by the fixing material 12, and the proximal portion of the second core wire 3 is fixed to the first core wire 2 by the fixing material 13. As a result, an intermediate portion between the distal portion and the proximal portion of the second core wire 3 is not fixed to the first core wire 2, but is in a state of being in contact with the first core wire 2. Based on this configuration, when the distal portion of the guide wire 1 is bent, flexibility at the distal side of the guide wire 1 is obtained because the unfixed regions of the first core wire 2 and the second core wire 3 are bent independently as compared with a case where the overall second core wire 3 is fixed to the first core wire 2 by bonding (i.e., the first and second core wires 2, 3 are bonded to one another along their axial extents). The degree of freedom of shaping is improved by leaving the first core wire 2 and the second core wire 3 unfixed in the intermediate portion between the fixing materials 12, 13 at the distal and proximal portions, respectively. Further, the abutting resistance of the guide wire 1 can also be reduced based on this configuration. The "abutting resistance" is the hardness when the distal end of the guide wire 1 abuts against the blood vessel wall. When the abutting resistance is high, there is a risk of piercing of the blood vessel wall with the guide wire 1. Since the abutting resistance of the guide wire 1 disclosed here is relatively low based on the above described configuration, it is possible to prevent or suppress the risk.

On the other hand, the first core wire 2 and the second core wire 3 may be fixed to each other at select positions (e.g., spaced apart or continuous sections in the axial direction). The rigidity or the torque transmission performance of the guide wire 1 can be selectively changed, by changing the place where the fixation is performed or the number of fixing points. For example, in addition to the fixation using the fixing material 12 and the fixing material 13, the entire third linear portion 33 can be fixed to the first core wire 2. When the entirety of the third linear portion 33 is fixed to the first core wire 2, the torque transmission performance of the guide wire 1 is improved. As another fixing aspect, for example, there may be fixation at the boundary portion between the first plate-shaped portion 21 and the second plate-shaped portion 32, fixation of the first plate-shaped portion 21 of the first core wire 2 and the second linear portion 31 of the second core wire 3, fixation of the first linear portion 22 of the first core wire 2 and the second plate-shaped portion 32 of the second core wire 3, and the like. By appropriately selecting the fixations, it is possible to provide a highly flexible guide wire 1, a guide wire 1 having a high torque transmission performance, and/or a guide wire 1 having excellent shaping property, depending on various operations. Examples of the fixation include a method of welding, a method of adhesion using solder (brazing filler metal) or an adhesive, and the like.

The second plate-shaped portion 32 is a flat plate in a natural state before being shaped similar to the first plate-shaped portion 21. A normal line $N_{21}$ of the first plate-shaped portion 21 and a normal line $N_{32}$ of the second plate-shaped portion 32 in the natural state are directed in the same direction as shown in FIG. 1. That is, the thickness direction (i.e., a direction orthogonal to the axial direction and perpendicular to the width direction) of the first plate-shaped portion 21 and the thickness direction of the second plate-shaped portion 32 are directed in the same direction (i.e., the horizontal directions of the first and second plate-shaped portions 21, 32 are parallel to one another). Therefore, for example, the operation of superimposing the first core wire 2 and the second core wire 3 at the time of manufacturing the guide wire 1 becomes relatively easy. Additionally, the two-dimensional shaping of the guide wire 1 can be easily performed. The shaping of the guide wire 1 is performed by bending the guide wire 1 in the normal direction of the first plate-shaped portion 21 or the second plate-shaped portion 32. Accordingly, when the normal line $N_{21}$ of the first plate-shaped portion 21 and the normal line $N_{32}$ of the second plate-shaped portion 32 are directed in the same direction, the bending directions of the first plate-shaped portion 21 and the second plate-shaped portion 32 are identical to each other. This alignment of bending directions is preferable in performing the two-dimensional shaping, for example, in a case where the first bent portion and the second bent portion are provided on the guide wire 1 to perform the shaping of the two-stage shape, since it is possible to provide the first bent portion and the second bent portion on the same plane including the long axis of the guide wire 1.

The cross-sectional shape of the first linear portion 22 is semicircular as described above. Therefore, the first linear portion 22 has one side surface 221 curved in a semicircular arc shape, and a second side surface shaped as a flat side surface 222 as shown in FIG. 1. By making the flat side surface 222 (among the side surface 221 and the side surface 222) face the second plate-shaped portion 32, the first linear portion 22 and the second plate-shaped portion 32 enter a state of stably overlapping each other (i.e., the flat surface of the first linear portion 22 may directly contact the flat side surface of the second plate-shaped portion 32 as shown in FIG. 1).

The second plate-shaped portion 32 has a gradually decreasing width portion 321 having a width $W_{32}$ gradually decreasing (tapering) toward the distal side formed at the distal portion as shown in FIG. 2. In addition, the second plate-shaped portion 32 has a gradually decreasing width portion 323 having the width $W_{32}$ gradually decreasing toward the proximal side formed at the proximal portion as shown in FIG. 2. An intermediate portion between the gradually decreasing width portion 321 and the gradually decreasing width portion 323 is a constant width portion 322 in which the width $W_{32}$ is constant along the longitudinal direction of the wire. In the present embodiment, the width $W_{32}$ at the constant width portion 322 is the same as the width $W_{21}$ of the first plate-shaped portion 21. However, the width $W_{32}$ of the constant width portion 322 is not limited to being equal to the width $W_{21}$ of the first plate-shaped portion 21, and the width $W_{32}$ may be greater than the width $W_{21}$.

The thickness $t_{32}$ of the second plate-shaped portion 32 is constant along the longitudinal direction of the wire, similar to the thickness $t_{21}$ of the first plate-shaped portion 21 being constant along the longitudinal direction of the wire. In the present embodiment, the thickness $t_{32}$ is the same as the thickness $t_{21}$ of the first plate-shaped portion 21. But the thickness $t_{32}$ of the second plate-shaped portion 32 is not limited to being the same as the thickness $t_{21}$ of the first plate-shaped portion 21. For example, the thickness $t_{32}$ may be thinner (smaller) than the thickness $t_{21}$. Further, the thickness $t_{32}$ is not limited to being constant along the longitudinal direction of the wire, but may, for example, gradually decrease (taper) toward the distal end in the axial direction.

The overall length $L_{32}$, the width $W_{32}$ and the thickness $t_{32}$ have the above-described sizes, and the overall length $L_{21}$, the width $W_{21}$ and the thickness $t_{21}$ also have the above-mentioned sizes. By appropriately combining the respective sizes, it is possible to obtain the guide wire 1 having different degrees of shaping, depending on various desired operations using the guide wire 1.

As illustrated in FIG. 1, a distal end 324 (distal portion) of the second plate-shaped portion 32 is in contact with a proximal end 214 (proximal portion) of the adjacent first plate-shaped portion 21 on the distal side thereof (e.g., as shown in the plan view of FIG. 1). As a result, the second plate-shaped portion 32 is in a state of being disposed on the distal side as much as possible (i.e., the second plate-shaped portion 32 is urged proximally by the first plate-shaped portion 21). In such an arrangement, the first plate-shaped portion 21 and the second plate-shaped portion 32 form apparently continuous plate-shaped portions (i.e., the first plate-shaped portion 21 and the second plate-shaped portion 32 appear to be continuous to one another, although the plate-shaped portions 21, 32 are each part of separate core wires 2, 3). Therefore, it is possible to form a (relatively) long shapeable region of the guide wire 1. Generally, the shaping is preferably performed at the distal portion of the guide wire 1. Therefore, a state preferable for shaping is obtained by disposing the second plate-shaped portion 32 on the distal side as much as possible.

In addition, the gradually decreasing width portion 321 formed on the distal side of the second plate-shaped portion 32 and the gradually decreasing width portion 213 formed on the proximal side of the first plate-shaped portion 21 can work together to reliably prevent the end portions of the second plate-shaped portion 32 and the first plate-shaped portion 21 from biting each other, for example, when the shaping is performed on the second plate-shaped portion 32. That is, biting may occur if the first plate-shaped portion 21 and the second plate-shaped portion 32 are caught/stuck due to undesirable abutting and/or contact between the first plate-shaped portion 21 and the second plate shaped portion 32 that causes the guide wire to deform into an unintended shape. If this situation occurs, the maneuverability of the guide wire may be reduced. Therefore, it is possible to help prevent the second plate-shaped portion 32 and the first plate-shaped portion 21 from being undesirably shaped by providing the gradually decreasing width portion 321 on the distal side of the second plate-shaped portion 32 and the gradually decreasing width portion 213 on the proximal side of the first plate-shaped portion 21.

The length $L_{10}$ from the distal end 211 of the first plate-shaped portion 21 to the proximal end 325 of the second plate-shaped portion 32 along the longitudinal direction of the wire is preferably 0.5 mm or more and 250 mm or less (between 0.5 mm and 250 mm), more preferably 0.5 mm or more and 100 mm or less, and even more preferably 0.5 mm or more and 50 mm or less. This contributes to achieving both the torque transmission performance and the shaping property.

The second linear portion 31 is provided continuously on the distal side of the second plate-shaped portion 32 (i.e., the proximal end of the second linear portion 31 is connected to the distal end of the second plate-shaped portion 32 so that the second linear portion 31 is continuous with the second plate-shaped portion 32). The second linear portion 31 is a portion having a linear shape that is thinner (i.e., smaller in the width direction) than the second plate-shaped portion 32. The second linear portion 31 is disposed to overlap the first plate-shaped portion 21 in the axial direction. That is, the second linear portion 31 is in contact with the first plate-shaped portion 21 on the same side surface as the side surface on which the second plate-shaped portion 32 contacts the first linear portion 22 where the second plate-shaped portion 32 axially overlaps the first linear portion 22.

In the present embodiment, the overall length $L_{31}$ of the second linear portion 31 is the same as the overall length $L_{21}$ of the first plate-shaped portion 21, but the present invention is not limited to the overall length $L_{31}$ of the second linear portion 31 being the same as the overall length $L_{21}$ of the first plate-shaped portion 21. The overall length $L_{31}$ may be, for example, shorter than the overall length $L_{21}$. When the overall length $L_{31}$ is shorter than the overall length $L_{21}$, a distal end 313 of the second linear portion 31 is fixed in the middle of the first plate-shaped portion 21 in the longitudinal direction.

As illustrated in FIG. 1, the cross-sectional shape of the second linear portion 31 is semicircular similar to the first linear portion 21 being semicircular as described above and also illustrated in FIG. 1. Therefore, the second linear portion 31 has a side surface 311 curved in a semicircular arc shape, and a flat side surface 312. By making the flat side surface 312 (i.e., the surface among the side surface 311 and the side surface 312) face the first plate-shaped portion 21, the first plate-shaped portion 21 and the second linear portion 31 enter a state of stably overlapping each other (i.e., the flat surface of the second linear portion 31 may directly contact the flat side surface of the first plate-shaped portion 21 as shown in FIG. 1). The radius $R_{31}$ of the second linear portion 31 shown in FIGS. 1-2 is constant along the longitudinal direction of the wire. The radius $R_{31}$ is not particularly limited, and may be, for example, the same as the thickness $t_{32}$.

The third linear portion 33 is provided continuously on the proximal side of the second plate-shaped portion 32 (i.e., the distal end of the third linear portion 33 is directly connected to the proximal end of the second plate-shaped portion 32 so that the second plate-shaped portion 32 and the third linear portion 33 are continuous with one another). The third linear portion 33 is a portion of the second core wire 3 having a linear shape that is thinner (smaller in the width direction) than the second plate-shaped portion 32. The third linear portion 33 is disposed to overlap the first linear portion 22 together with the second plate-shaped portion 32 in the axial direction, that is, to be in contact with the first linear portion 22 along the axial extent of the first linear portion 22. The third linear portion 33 thus separates the second plate-shaped portion 32 from the fixing material 13. Therefore, it is possible to prevent or suppress the influence of the fixation by the fixing material 13 on the second plate-shaped portion 32 at the time of shaping the second plate-shaped portion 32. Further, the third linear portion 33 contributes to reliably transmitting the torque (which is applied from the proximal side of the guide wire 1) to the second core wire 3. Furthermore, the torque applied from the proximal side of the guide wire 1 is transmitted to the first core wire 2 and the second core wire 3 without biasing since the third linear portion 33 is disposed to axially overlap the first linear portion 22.

As illustrated in FIG. 1, the cross-sectional shape of the third linear portion 33 is semicircular. Accordingly, the third linear portion 33 has a side surface 331 curved in a semicircular arc shape, and a flat side surface 332. By making the side surface 332 (i.e., the surface among the side surface 331 and the side surface 332) face the side surface 222 of the first linear portion 22, the third linear portion 33 and the first linear portion 22 enter a state of stably overlapping each other (i.e., the flat surface of the third linear portion 33 may directly contact the flat side surface of the first plate-shaped portion 21 as shown in FIG. 1). The radius $R_{33}$ of the third linear portion 33 shown in FIGS. 1-2 is constant along the longitudinal direction of the wire. The radius $R_{33}$ is not particularly limited, and is preferably, for example, the same as the radius $R_{22}$.

As described above, the cross-sectional shape of the first linear portion 22 and the cross-sectional shape of the second linear portion 31 each have a semicircular shape (i.e., the first linear portion 22 and the second linear portion 31 have equivalent cross-sectional shapes; the shapes are "equivalent" in that they possess the same shape and cross-sectional area, despite the cross-sectional shapes being oriented differently within the guide wire). A center $O_{22}$ of the semicircle in the first linear portion 22 and a center $O_{31}$ of the semicircle in the second linear portion 31 are coaxial (i.e., in a coaxial state positioned on the same one axis $AX_{10}$ along the longitudinal direction of the wire) to one another. In other words, the center $O_{22}$ and the center $O_{31}$ overlap each other when viewed from the distal end in the axial direction and the guide wire 1 is in the natural state. A center $O_{33}$ of the semicircle in the third linear portion 33 and the center $O_{22}$ of the semicircle in the first linear portion 22 are also in a coaxial state positioned on the axis $AX_{10}$. A "circle" is formed by the cross-sectional shape of the third linear portion 33 and the cross-sectional shape of the first linear portion 22 as shown in FIG. 1.

In combination of the respective coaxial states and the fact that the first linear portion 22 overlaps the second plate-shaped portion 32 in the axial direction and the third linear portion 33 and that the second linear portion 31 overlaps the first plate-shaped portion 21 in the axial direction, the torque is reliably transmitted to the distal end of the guide wire 1 when the torque is applied from the proximal side of the guide wire 1.

The guide wire 1 described above can thus achieve both (relatively) excellent torque transmission performance and (relatively) excellent shaping property.

Since the wire main body 10 of the guide wire 1 is formed by making the first core wire 2 and the second core wire 3 overlap each other, the breaking strength (i.e., rupture strength) is improved (e.g., the plate-shaped portion of a core wire may be more likely to break/rupture because it is relatively thin; the wire main body 10 disclosed here is relatively less susceptible to rupture (i.e., possesses a higher rupture strength) because the first core wire 2 and the second core wire 3 overlap one another).

The constituent materials of the first core wire 2 and the second core wire 3 are not particularly limited. The material of the first and/or second core wire 2, 3 may include various metal materials such as alloys exhibiting pseudoelasticity including superelastic alloys, such as stainless steel, piano wire, cobalt type alloy, and nickel titanium alloy. When a superelastic alloy is used as the constituent material of the first core wire 2 and the second core wire 3, a treatment for eliminating superelasticity of a portion relating to shaping may be performed in order to improve the shaping property. The shaping portion means the first plate-shaped portion 21 and the first linear portion 22 of the first core wire 2 and the entire second core wire 3 (i.e., from the second linear portion 31 of the second core wire 3 to the third linear portion 33). Heat treatment and cold working may be used as such a treatment for helping to eliminate the superelasticity. The first core wire 2 and the second core wire 3 may be made of different materials than one another, but it is preferable that the first core wire 2 and the second core wire 3 are made of the same material or the same kind of material.

The outer diameters of the linear portions of the first core wire 2 and the second core wire 3 are not particularly limited and can be outer diameters that are suitable for a guide wire that is to be inserted into a living body. The outer diameters of the linear portions of the first core wire 2 and the second core wire 3 may be, for example, 40 µm to 360 µm.

The guide wire 1 may include a coil 11 which covers the first plate-shaped portion 21 and the first linear portion 22 of the first core wire 2, and covers the entire second core wire 3 (i.e., from the second linear portion 31 of the second core wire 3 to the third linear portion 33) as shown in FIG. 1. Like the second core wire 3, the coil 11 is fixed to the first core wire 2 via the fixing material 12 and the fixing material 13. By installing such a coil 11, for example, the contact area of the surface of the wire main body 10 in a living body is reduced, and the sliding resistance can be reduced. The operability of the guide wire 1 is thus further improved.

The coil 11 of FIG. 1 is formed by winding an element wire 111 around the wire main body 10. The element wires 111 adjacent to each other in the longitudinal direction (axial direction) of the guide wire 1 are in contact with each other in a natural state, namely, a so-called close winding state. The guide wire 1 is not limited to such a close winding configuration, however, and may have a rough winding portion in which the adjacent element wires 111 are spaced apart from each other.

It is preferable that at least the second plate-shaped portion 32 is spaced apart from the coil 11 (i.e., in the width and thickness directions), regardless of whether or not the shaping is performed. Therefore, the degree of freedom of shaping in the second plate-shaped portion 32 can be sufficiently maintained.

It is preferable that at least the outer peripheral portion of the coil 11 of the guide wire 1 is coated with a hydrophilic material. As a result, the hydrophilic material is wetted to produce lubricity, the sliding resistance of the guide wire 1 is reduced, and the slidability is improved. Therefore, the operability of the guide wire 1 is improved. As the hydrophilic material, for example, it is possible to use a cellulose-based polymer substance, a polyethylene oxide-based polymer substance, a maleic anhydride-based polymer substance (for example, a maleic anhydride copolymer such as methyl vinyl ether-maleic anhydride copolymer), an acrylamide-based polymer material (for example, a polyacrylamide, a polyglycidyl methacrylate-dimethyl acrylamide (PGMA-DMAA) block copolymer), water-soluble nylon, polyvinyl alcohol, polyvinyl pyrrolidone, and the like.

Second Embodiment

Figure 3:
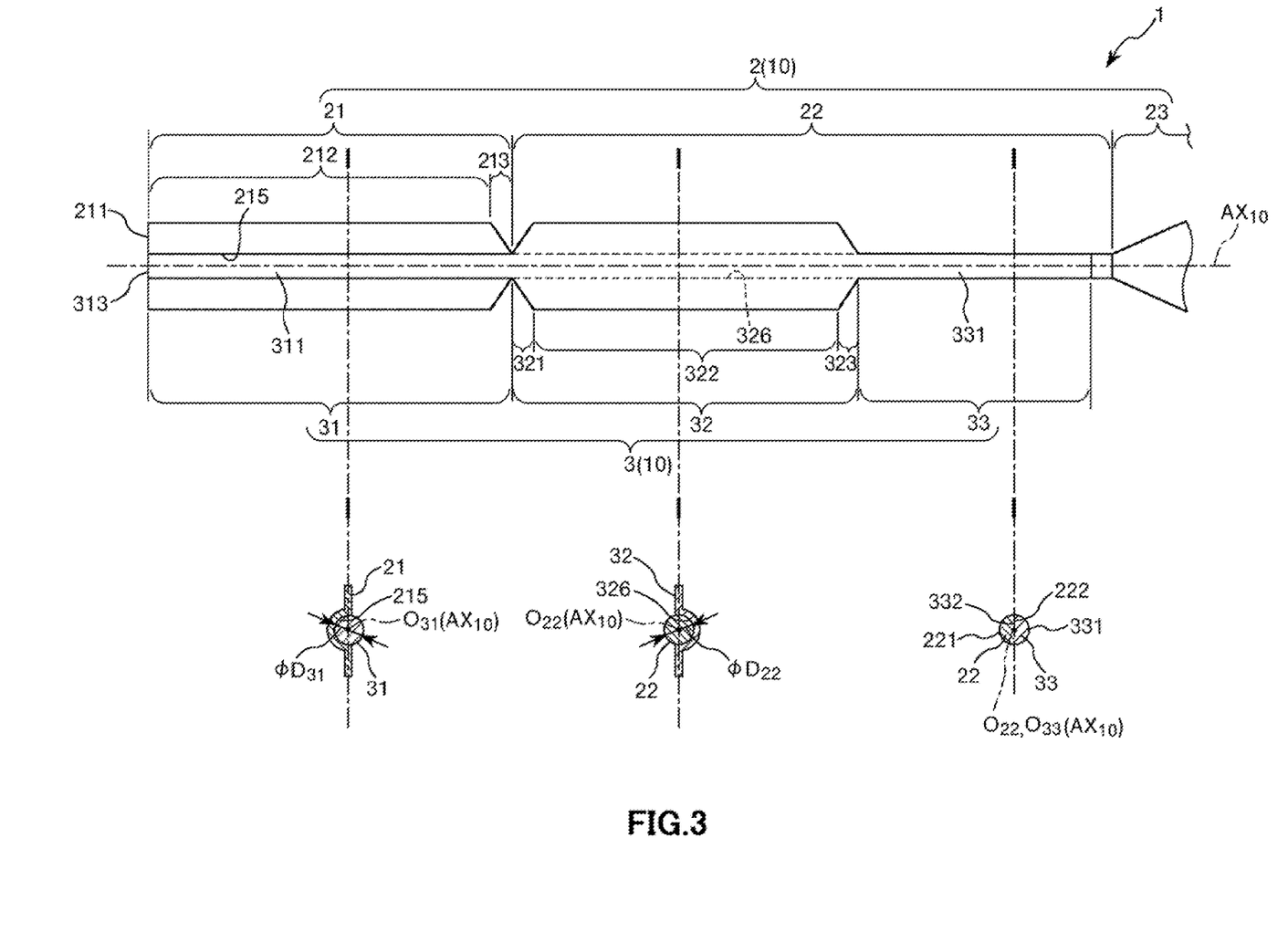
FIG. 3 is a plan view and auxiliary cross-sectional views of the first core wire and the second core wire provided in a second embodiment of the disclosed guide wire.

FIG. 3 shows a plan view and three auxiliary cross-sectional views of a first core wire and a second core wire included in another embodiment of the disclosed guide wire (the second embodiment).

Hereinafter, the second embodiment of the disclosed guide wire is described with reference to FIG. 3, but the differences from the above-described embodiment is mainly described, and the description of the same matter is not be provided.

The embodiment shown in FIG. 3 is the same as the first embodiment except that the embodiment of FIG. 3 has a positioning portion that helps maintain the coaxial state of the core wires 2 and 3.

As illustrated in FIG. 3, the cross-sectional shape of the portion of the first linear portion 22 axially overlapping the second plate-shaped portion 32 is circular. The cross-sectional shape of the second linear portion 31 is also circular. It is preferable that an outer diameter $\phi D_{22}$ of the first linear portion 22 (having a circular shape) and an outer diameter $\phi D_{31}$ of the second linear portion 31 have the same size.

A first groove 215 is formed in the first plate-shaped portion 21 along the longitudinal direction of the wire as shown in FIG. 3. The first groove 215 is formed by bending and plastically deforming the first plate-shaped portion 21 by, for example, a pressing machine. Then, the second linear portion 31 can be inserted into (positioned in) the first groove 215.

A second groove 326 is formed in the second-plate shaped portion 32 along the longitudinal direction of the wire. Like the first groove 215, the second groove 326 is also formed by bending and plastically deforming the second plate-shaped portion 32 by, for example, a pressing machine. The first linear portion 22 can then be inserted into (positioned in) the second groove 326.

By the insertion as described above, the center $O_{22}$ of the circle in the first linear portion 22 and the center $O_{31}$ of the circle in the second linear portion 31 are in a coaxial state positioned on the axis $AX_{10}$, and the coaxial state can be reliably maintained. As a result, it is possible to reliably improve torque transmission performance.

In the guide wire 1 of the present embodiment, the first groove 215 and the second groove 326 function as positioning portions that maintain the coaxial state.

Third Embodiment

Figure 4:
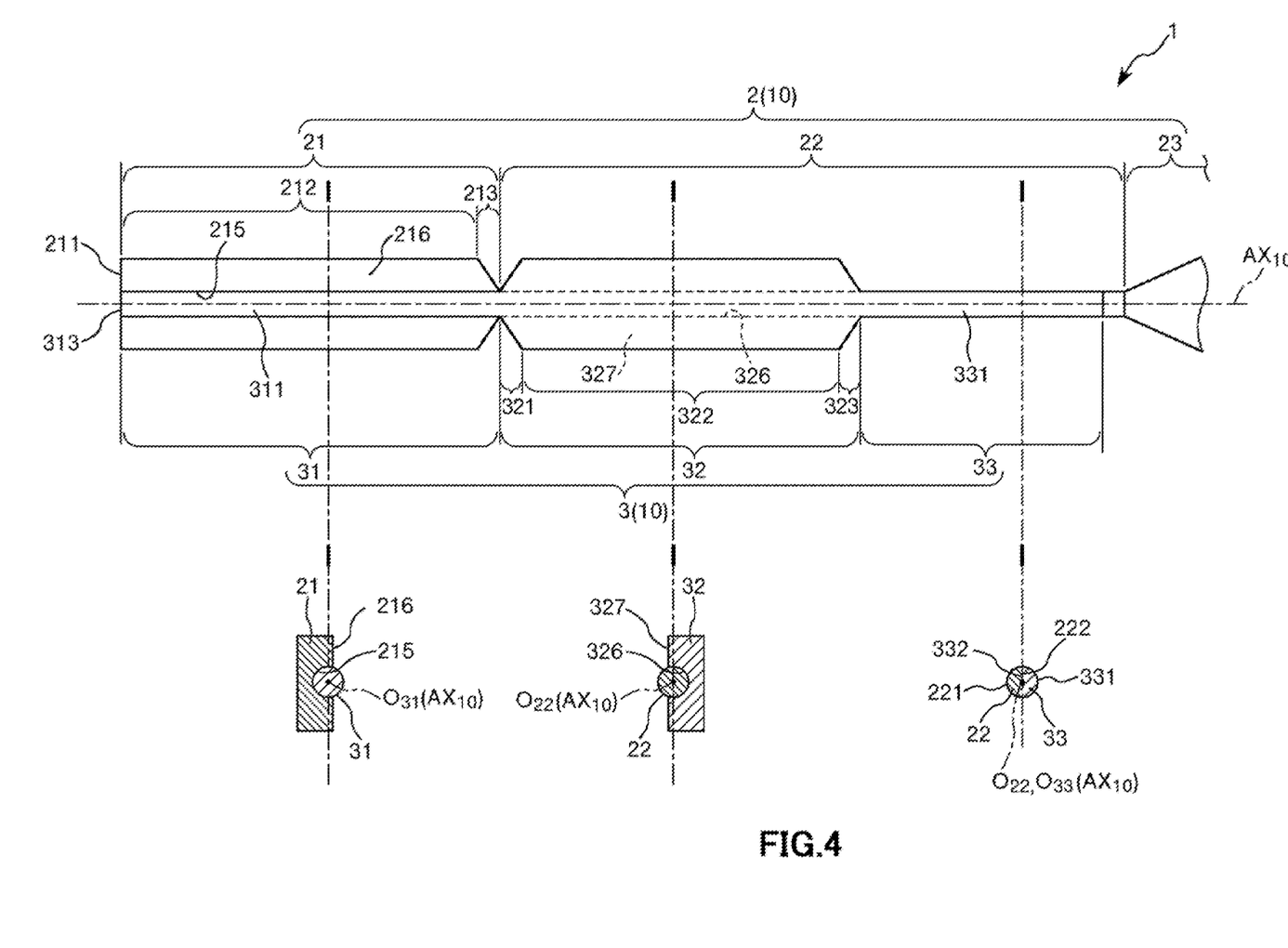
FIG. 4 is a plan view and auxiliary cross-sectional views of the first core wire and the second core wire provided in a third embodiment of the disclosed guide wire.

FIG. 4 depicts a plan view and auxiliary cross-sectional views of a first core wire and a second core wire included in another embodiment of the disclosed guide wire (a third embodiment).

Hereinafter, the third embodiment of the guide wire of the present invention will be described with reference to the drawing, but the differences from the above-described embodiment will be mainly described, and the description of the same matter will not be provided.

This embodiment is the same as the embodiments described above except that the method of forming the first groove in the first plate-shaped portion 21 and the second groove in the second plate-shaped portion 32 is different.

In the present embodiment illustrated in FIG. 4, the first groove 215 is formed by cutting a surface 216 of the first plate-shaped portion 21 facing the second linear portion 31 side by, for example, a cutting machine. As a result, since the first groove 215 can be provided as a groove having a size large enough to fit the second linear portion 31, the second linear portion 31 is prevented from being detached from the first groove 215 (i.e., the second linear portion 31 remains within the first groove 215).

The second groove 326 is also formed by cutting a surface 327 of the second plate-shaped portion 32 facing the first linear portion 22 side by, for example, a cutting machine. Accordingly, since the second groove 326 can be provided as a groove having a size large enough to fit the first linear portion 22, the first linear portion 22 is prevented from being detached from the second groove 326 (i.e., the first linear portion 22 remains within the second groove 316).

Fourth Embodiment

Figure 5:
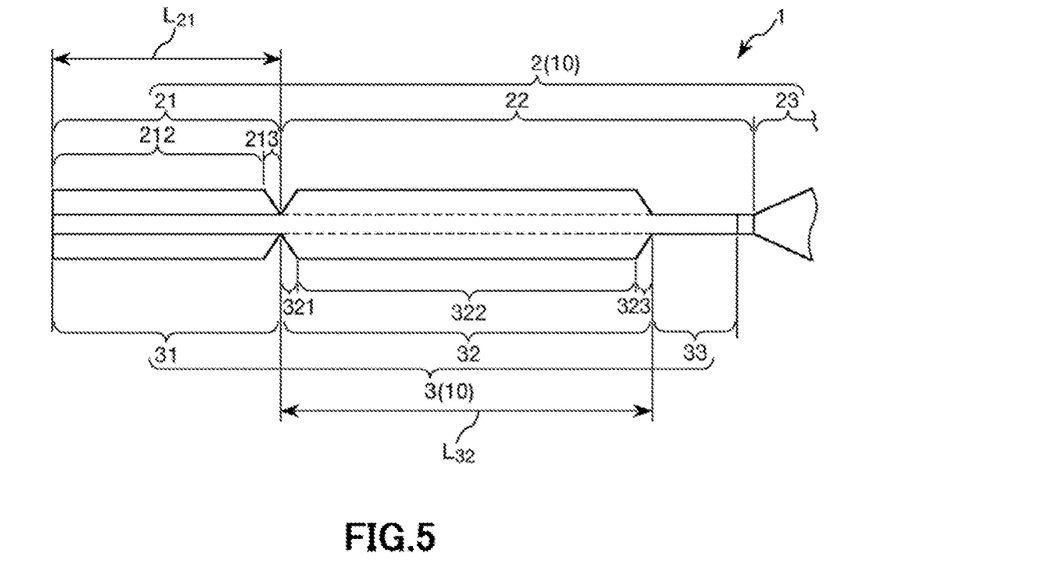
FIG. 5 is a plan view of the first core wire and the second core wire provided in a fourth embodiment of the disclosed guide wire.

FIG. 5 is a plan view of a first core wire and a second core wire of another embodiment of the disclosed guide wire (a fourth embodiment).

Hereinafter, the fourth embodiment of the guide wire of the present invention will be described with reference to the drawing, but the differences from the above-described embodiment will be mainly described, and the description of the same matter will not be provided.

This embodiment is the same as the first embodiment except that a magnitude relation between the overall length of the first plate-shaped portion and the overall length of the second plate-shaped portion is different.

In the embodiment shown in FIG. 5, the overall length $L_{32}$ of the second plate-shaped portion 32 is longer than the overall length $L_{21}$ of the first plate-shaped portion 21. This makes it (relatively) easier to perform the shaping on the second plate-shaped portion 32.

Fifth Embodiment

Figure 6:
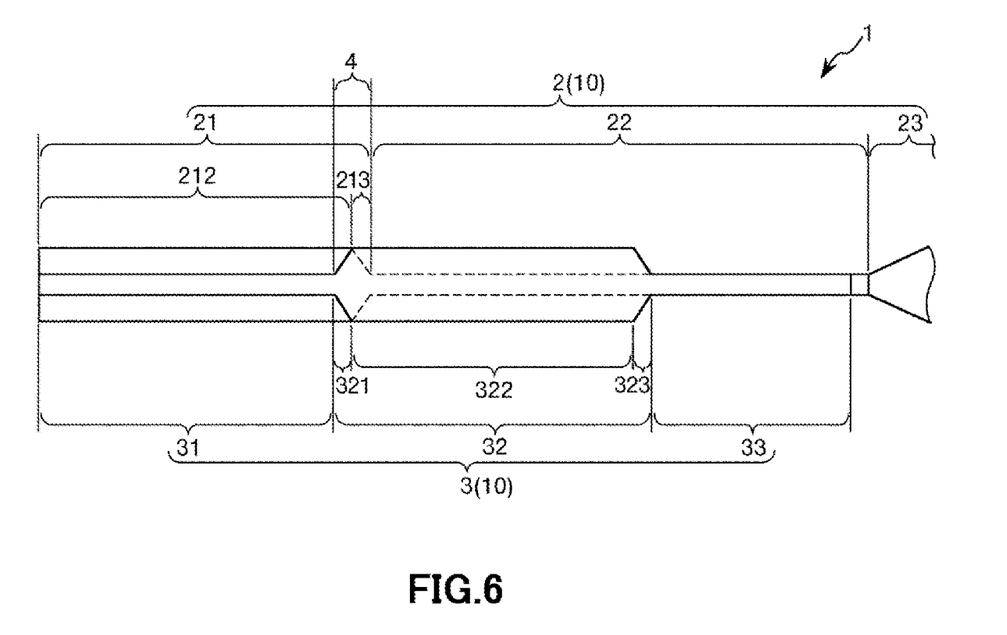
FIG. 6 is a plan view of the first core wire and the second core wire of a fifth embodiment of the disclosed guide wire.

FIG. 6 is a plan view of a first core wire and a second core wire of another embodiment of the disclosed guide wire (a fifth embodiment).

Hereinafter, the fifth embodiment of the guide wire of the present invention will be described with reference to the drawing, but the differences from the above-described embodiment will be mainly described, and the description of the same matter will not be provided.

This embodiment is the same as the first embodiment except that a positional relation between the first plate-shaped portion 21 and the second plate-shaped portion 32 is different.

As shown in the FIG. 6 embodiment, an overlapping portion 4 is formed in which a proximal portion of the first plate-shaped portion 21 (including the proximal end) and a distal portion of the second plate-shaped portion 32 (including the distal end) overlap in the axial direction. Torque is (relatively) smoothly transmitted from the second plate-shaped portion 32 to the first plate-shaped portion 21 at the overlapping portion 4. Therefore, the torque transmission performance is improved.

Sixth Embodiment

Figure 7:
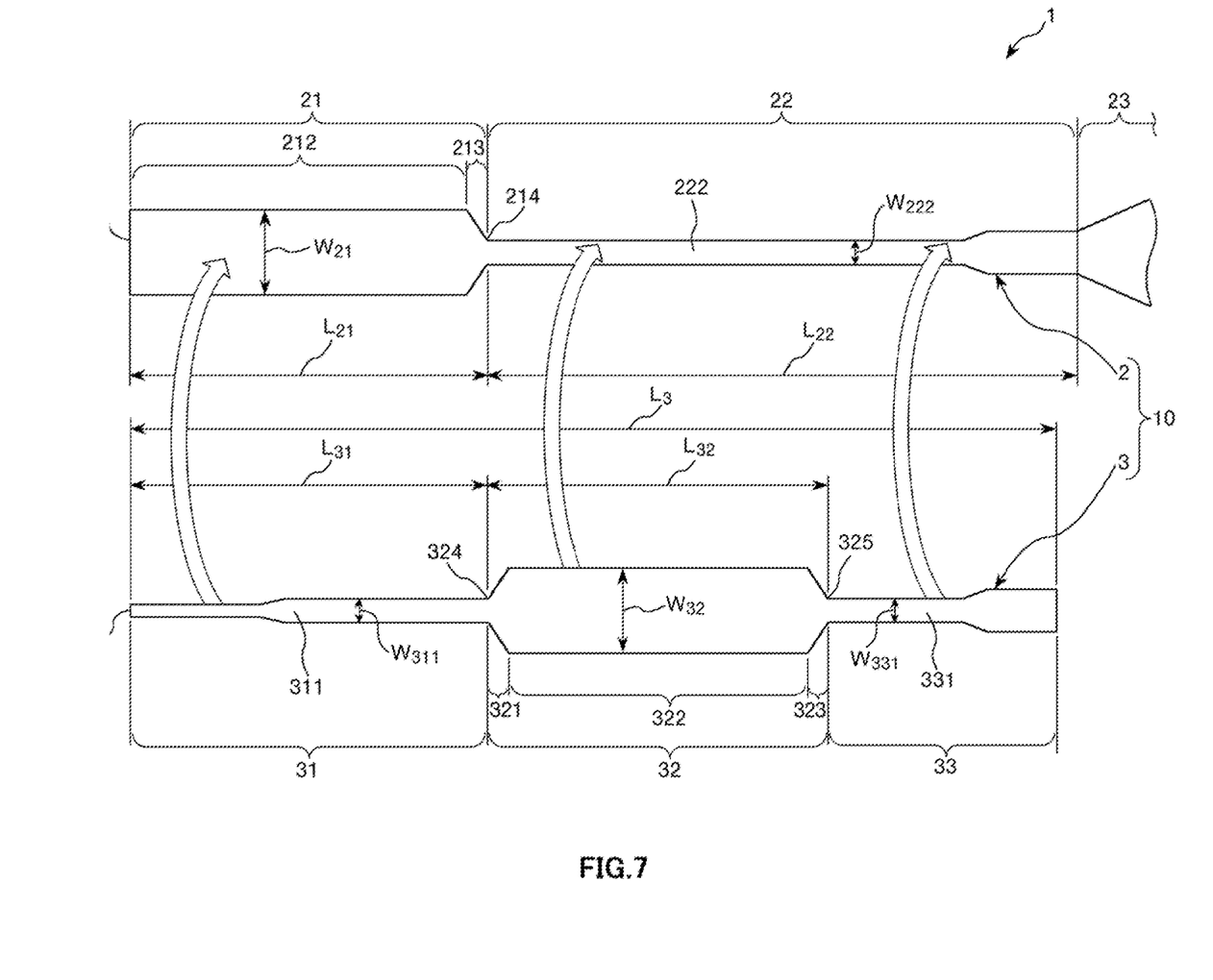
FIG. 7 is an exploded plan view of the first core wire and the second core wire of a sixth embodiment of the disclosed guide wire.

FIG. 7 is an exploded plan view of a first core wire and a second core wire of another embodiment of the disclosed guide wire (a sixth embodiment).

Hereinafter, the sixth embodiment of the guide wire of the present invention will be described with reference to the drawing, but the differences from the above-described embodiment will be mainly described, and the description of the same matter will not be provided.

This embodiment is the same as the first embodiment except that the shapes of the first core wire and the second core wire are different from each other.

In the embodiment shown in FIG. 7, a width $W_{222}$ of the side surface 222 of the first linear portion 22 of the first core wire 2 decreases stepwise toward the distal side. In the third linear portion 33 of the second core wire 3, a width $W_{331}$ of the side surface 331 also decreases stepwise toward the distal side, corresponding to the shape of the first linear portion 22. It is preferable that the cross-sectional shape of the first linear portion 22 and the cross-sectional shape of the third linear portion 33 together form a "circle".

In addition, a width $W_{311}$ of the side surface 311 of the second linear portion 31 of the second core wire 3 also decreases stepwise toward the distal side.

The guide wire 1 thus gradually decreases in rigidity toward the distal side as a whole by having the shape as described above and show in FIG. 7. As a result, the guide wire 1 has, for example, good flexibility at the distal portion, and the followability (maneuverability) to the blood vessel or the like and safety are improved.

The width $W_{222}$, the width $W_{311}$, and the width $W_{331}$ decrease stepwise toward the distal side as described above, and the number of stages is one in the illustrated configuration. However, but the number of stages (i.e., the number of additional stepwise width-decreasing portions) is not limited to one extra stage and may be plural stages (i.e., there may be any number of portions with widths decreasing in the stepwise manner as shown in FIG. 7).

Each of the width $W_{222}$, the width $W_{311}$, and the width $W_{331}$ may, for example, continuously decrease toward the distal side, in addition to the stepwise decrease toward the distal side (i.e., the widths $W_{222}$, $W_{311}$, and $W_{331}$ may have outer diameters that gradually decrease in a tapered manner towards the distal end).

Although the disclosed guide wire has been described with reference to example embodiments illustrated in the drawings, the inventive guide wire is not limited thereto, and each part constituting the guide wire may be substituted for any configuration capable of exerting the same function. Also, additional, desirable components may be added.

The guide wire disclosed here may also include a combination of two or more configurations (or features) among the above described embodiments.

Although a single second core wire is shown and described in each of the above embodiments, the second core wire is not limited to being a single wire. For example, plural second core wires may be used. For example, in a case where the number of second core wires is two, the guide wire can be one in which the first core wire is disposed between the two second core wires.

Although a magnitude relation between the overall length of the first core wire and the overall length of the second core wire is set such that the overall length of the first core wire is longer than the overall length of the second core wire in each of the above embodiments, the disclosed guide wire is not limited to having a longer first core wire. For example, the overall length of the second core wire may be longer than the overall length of the first core wire.

The first core wire may further include a linear portion having a liner shape that is provided continuously on the distal side of the first plate-shaped portion and is thinner (smaller in the width direction) than the first plate-shaped portion.

In some embodiments, the gradually decreasing width portion can be omitted in the first core wire and the second core wire.

The third linear portion can be omitted from the second core wire in some embodiments. In this case, it is preferable that the cross-sectional shape of the portion of the first linear portion of the first core wire overlapping the third linear portion is circular.

INDUSTRIAL APPLICABILITY

The disclosed guide wire includes a flexible first core wire and a flexible second core wire configured separately from the first core wire. The first core wire has a first plate-shaped portion having a plate shape, and a first linear portion provided continuously to the proximal side of the first plate-shaped portion and having a linear shape thinner than the first plate-shaped portion. The second core wire has a second plate-shaped portion having a plate shape and disposed to axially overlap the first linear portion, and a second linear portion that is provided continuously on the distal side of the second plate-shaped portion, has a linear shape thinner than the second plate-shaped portion, and is disposed to axially overlap the first plate-shaped portion. Therefore, it is possible to achieve (relatively) excellent compatibility between the torque transmission performance and the shaping property. Therefore, the guide wire has industrial applicability.

The detailed description above describes a guide wire. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
    a flexible first core wire comprising a first plate-shaped portion having a plate shape and a first linear portion having a linear shape, the first core wire extending in an axial direction, the first plate-shaped portion possessing a distal end and a proximal end opposite the distal end in the axial direction, the first linear portion possessing a distal end and a proximal end opposite the distal end in the axial direction, the distal end of the first linear portion being connected to the proximal end of the first plate-shaped portion so that the first plate-shaped portion and the first linear portion are continuous with one another, the first plate-shaped portion having an intermediate portion between and spaced from the distal and proximal ends of the first plate-shaped portion, the first linear portion having an intermediate portion between and spaced from the distal and proximal ends of the first linear portion;
    the first plate-shaped portion possessing a width in a width direction orthogonal to the axial direction and the first linear portion possessing a width in the width direction, the width of the first plate-shaped portion being greater than the width of the first linear portion so that the first linear portion is thinner than the first plate-shaped portion;
    a flexible second core wire comprising a second plate-shaped portion having a plate shape and a second linear portion having a linear shape, the second plate-shaped portion possessing a distal end and a proximal end opposite the distal end in the axial direction, the second linear portion possessing a distal end and a proximal end opposite the distal end in the axial direction, the distal end of the second plate-shaped portion being connected to the proximal end of the second linear portion so that the second plate-shaped portion and the second linear portion are continuous with one another;
    the second plate-shaped portion possessing a width in the width direction and the second linear portion possessing a width in the width direction, the width of the second plate-shaped portion being greater than the width of the second linear portion so that the second linear portion is thinner than the second plate-shaped portion, the second plate-shaped portion having an intermediate portion between and spaced from the distal and proximal ends of the second plate-shaped portion, the second linear portion having an intermediate portion between and spaced from the distal and proximal ends of the second linear portion; and
    the second plate-shaped portion axially overlapping the first linear portion so that the intermediate portion of the second plate-shaped portion and the intermediate portion of the first linear portion directly contact one another, and the intermediate portion of the second linear portion directly contacting the intermediate portion of the first plate-shaped portion.

2. The guide wire according to claim 1, wherein
    the second core wire is shorter than the first core wire, the second core wire possessing a distal portion and a proximal portion, and
    at least the distal portion and the proximal portion of the second core wire are fixed to the first core wire.

3. The guide wire according to claim 1, wherein a length from the distal end of the first plate-shaped portion to the proximal end of the second plate-shaped portion along a longitudinal direction of the wire is between 0.5 mm and 250 mm.

4. The guide wire according to claim 1, wherein the first plate-shaped portion and the second plate-shaped portion each possess a cross section of a flat plate in a natural state in which no external force is applied, and the first plate-shaped portion and the second plate-shaped portion have surfaces parallel to one another in a thickness direction, the thickness direction being orthogonal to the axial direction and perpendicular to the width direction.

5. The guide wire according to claim 1, wherein a center of a cross-sectional shape of the first linear portion and a center of a cross-sectional shape of the second linear portion are coaxial to one another along a longitudinal direction of the wire.

6. The guide wire according to claim 5, further comprising:
    a positioning portion which maintains the first linear portion and the second linear portion as coaxial to one another.

7. The guide wire according to claim 6, wherein the positioning portion includes a first groove formed in the first plate-shaped portion and into which the second linear portion is positioned, and a second groove formed in the second plate-shaped portion and into which the first linear portion is positioned.

8. The guide wire according to claim 1, wherein the first linear portion possess a cross-sectional shape and the second linear portion possess a cross-sectional shape, the cross-sectional shape of the first linear portion and the cross-sectional shape of the second linear portion being a common shape.

9. The guide wire according to claim 1, wherein
a cross-sectional shape of the first linear portion is circular or semicircular, and
a cross-sectional shape of the second linear portion is circular or semicircular.

10. The guide wire according to claim 1, wherein the second core wire has a third linear portion that is provided continuously on the proximal side of the second plate-shaped portion, the third linear portion possessing a linear shape that has a width in the width direction smaller than the width of the second plate-shaped portion so that the third linear portion is thinner than the second plate-shaped portion, the third linear portion overlapping the first linear portion in the axial direction.

11. The guide wire according to claim 1, wherein the first core wire and the second core wire are fixed to one another by a solder or brazing material.

12. A guide wire comprising:
a first core wire comprising a first plate-shaped portion having a plate shape and a first linear portion having a linear shape, the first core wire extending in an axial direction, the first plate-shaped portion possessing a distal end and a proximal end opposite the distal end in the axial direction, the first linear portion possessing a distal end and a proximal end opposite the distal end in the axial direction, the distal end of the first linear portion being connected to the proximal end of the first plate-shaped portion so that the first plate-shaped portion and the first linear portion are continuous with one another, the first plate-shaped portion having an intermediate portion between and spaced from the distal and proximal ends of the first plate-shaped portion, the first linear portion having an intermediate portion between and spaced from the distal and proximal ends of the first linear portion;
the first plate-shaped portion possessing a cross-sectional shape and the first linear portion possessing a cross-sectional shape, at least one dimension of the cross-sectional shape of the first linear portion being smaller than at least one dimension of the cross-sectional shape of the first plate-shaped portion;
a second core wire comprising a second plate-shaped portion having a plate shape and a second linear portion having a linear shape, the second plate-shaped portion possessing a distal end and a proximal end opposite the distal end in the axial direction, the second linear portion possessing a distal end and a proximal end opposite the distal end in the axial direction, the distal end of the second plate-shaped portion being connected to the proximal end of the second linear portion so that the second plate-shaped portion and the second linear portion are continuous with one another, the second plate-shaped portion having an intermediate portion between and spaced from the distal and proximal ends of the second plate-shaped portion, the second linear portion having an intermediate portion between and spaced from the distal and proximal ends of the second linear portion;
the second plate-shaped portion possessing a cross-sectional shape and the second linear portion possessing a cross-sectional shape, at least one dimension of the cross-sectional shape of the second linear portion being smaller than at least one dimension of the cross-sectional shape of the second plate-shaped portion;
the second plate-shaped portion axially overlapping the first linear portion so that the intermediate portion of the second plate-shaped portion and the intermediate portion of the first linear portion directly contact one another, and the second linear portion axially overlapping the first plate-shaped portion so that the intermediate portion of the first plate-shaped portion and the intermediate portion of the second linear portion directly contact one another; and
the cross-sectional shape of the first plate-shaped portion is equivalent to the cross-sectional shape of the second plate-shaped portion, and the cross-sectional shape of the first linear portion is equivalent to the cross-sectional shape of the second linear portion.

13. The guide wire according to claim 12, wherein
the distal end of the first plate-shaped portion of the first core wire is fixed to the distal end of the second linear portion of the second core wire at a first fixing portion,
the proximal end of the first linear portion of the first core wire is fixed to the proximal end of the second core wire at a second fixing portion, and
the first core wire and the second core wire are unfixed to one another between the first fixing portion and the second fixing portion.

14. The guide wire according to claim 12, wherein the second core wire is shorter than the first core wire in the axial direction.

15. The guide wire according to claim 12, wherein
the guide wire possesses a width direction orthogonal to the axial direction,
the guide wire possesses a thickness direction orthogonal to the axial direction and perpendicular to the width direction, and
the first linear portion is smaller than the first plate-shaped portion in the width direction, the second linear portion is smaller than the second plate-shaped portion in the width direction, and
the first linear portion, the first plate-shaped portion, the second linear portion, and the second plate-shaped portion have the same thickness in the thickness direction.

16. The guide wire according to claim 12, wherein
the first plate-shaped portion comprises a groove and the second linear portion is positioned in the groove of the first plate-shaped portion, and
the second plate-shaped portion comprises a groove and the first linear portion is positioned in the groove of the second plate-shaped portion.

17. The guide wire according to claim 12, wherein the first core wire and the second core wire are fixed to one another by a solder or brazing material.

18. A guide wire comprising:
a first core wire comprising a first plate-shaped portion having a plate shape and a first linear portion having a linear shape, the first core wire extending in an axial direction, the first plate-shaped portion possessing a distal end and a proximal end opposite the distal end in the axial direction, the first linear portion possessing a distal end and a proximal end opposite the distal end in the axial direction, the distal end of the first linear portion being connected to the proximal end of the first plate-shaped portion so that the first plate-shaped portion and the first linear portion are continuous with one another, the first plate-shaped portion having an intermediate portion between and spaced from the distal and proximal ends of the first plate-shaped portion, the first linear portion having an intermediate portion between and spaced from the distal and proximal ends of the first linear portion;

the first plate-shaped portion possessing a cross-sectional shape and the first linear portion possessing a cross-sectional shape, at least one dimension of the cross-sectional shape of the first linear portion being smaller than at least one dimension of the cross-sectional shape of the first plate-shaped portion;

a second core wire comprising a second plate-shaped portion having a plate shape and a second linear portion having a linear shape, the second plate-shaped portion possessing a distal end and a proximal end opposite the distal end in the axial direction, the second linear portion possessing a distal end and a proximal end opposite the distal end in the axial direction, the distal end of the second plate-shaped portion being connected to the proximal end of the second linear portion so that the second plate-shaped portion and the second linear portion are continuous with one another, the second plate-shaped portion having an intermediate portion between and spaced from the distal and proximal ends of the second plate-shaped portion, the second linear portion having an intermediate portion between and spaced from the distal and proximal ends of the second linear portion;

the second plate-shaped portion possessing a cross-sectional shape and the second linear portion possessing a cross-sectional shape, at least one dimension of the cross-sectional shape of the second linear portion being smaller than at least one dimension of the cross-sectional shape of the second plate-shaped portion;

the second plate-shaped portion axially overlapping the first linear portion so that the intermediate portion of the second plate-shaped portion and the intermediate portion of the first linear portion directly contact one another and the second linear portion axially overlapping the first plate-shaped portion so that the intermediate portion of the first plate-shaped portion and the intermediate portion of the second linear portion directly contact one another;

the first core wire comprising a tapered portion possessing a distal end, the distal end of the tapered portion being connected to the proximal end of the first linear portion;

a proximal end of the second core wire being at the distal end of the tapered portion in the axial direction such that the second core wire is shorter than the first core wire; and the proximal end of the second core wire being fixed to the first core wire at a first fixation portion, the distal end of the first plate-shaped portion being fixed to the distal end of the second linear portion at a second fixation portion, and the first and second core wires being unfixed to one another between the first and second fixation portions.

19. The guide wire according to claim 18, wherein
the cross-sectional shape of the first plate-shaped portion is one of an entirely rectangular cross-section or a rectangular cross-section with a groove along one surface, and
the cross-sectional shape of the second plate-shaped portion is one of an entirely rectangular cross-section or a rectangular cross-section with a groove along one surface.

20. The guide wire according to claim 18, wherein the cross-sectional shape of the first plate-shaped portion is equivalent to the cross-sectional shape of the second plate-shaped portion, and the cross-sectional shape of the first linear portion is equivalent to the cross-sectional shape of the second linear portion.

21. The guide wire according to claim 18, wherein the first plate-shaped portion comprises a groove and the second linear portion is positioned in the groove of the first plate-shaped portion, and
the second plate-shaped portion comprises a groove and the first linear portion is positioned in the groove of the second plate-shaped portion.

22. The guide wire according to claim 21, wherein
the first plate-shaped portion transitions to the first linear portion at a first transition location such that the cross-sectional shape of the first core wire at the first transition location is a shape devoid of the groove; and
the second plate-shaped portion transitions to the second linear portion at a second transition location such that the cross-sectional shape of the second core wire at the second transition location is a shape devoid of the groove.

23. The guide wire according to claim 18, wherein the first fixation portion is a solder or brazing material, and the second fixation portion is a solder or brazing material.

* * * * *